United States Patent
Goetzen et al.

(10) Patent No.: US 8,992,600 B2
(45) Date of Patent: Mar. 31, 2015

(54) MARKER COMPOSITE AND MEDICAL IMPLANT COMPRISING AN X-RAY MARKER

(75) Inventors: Nils Goetzen, Rostock (DE); Anna Mirabelli, Rostock (DE); Andre Schoof, Bad Doberan (DE); Ullrich Bayer, Admannshagen-Bargeshagen (DE); Dirk Sadler, Rostock (DE); Johannes Riedmueller, Nuremberg (DE)

(73) Assignee: Biotronik AG, Buelach (CH)

( * ) Notice: Subject to any disclaimer, the term of this patent is extended or adjusted under 35 U.S.C. 154(b) by 0 days.

(21) Appl. No.: 13/288,512

(22) Filed: Nov. 3, 2011

(65) Prior Publication Data

US 2012/0116499 A1    May 10, 2012

Related U.S. Application Data

(60) Provisional application No. 61/410,976, filed on Nov. 8, 2010.

(51) Int. Cl.
*A61L 31/18* (2006.01)
*A61L 31/02* (2006.01)
*A61L 31/12* (2006.01)
*A61L 31/14* (2006.01)

(52) U.S. Cl.
CPC .............. *A61L 31/18* (2013.01); *A61L 31/022* (2013.01); *A61L 31/128* (2013.01); *A61L 31/148* (2013.01)
USPC ........................................ 623/1.34

(58) Field of Classification Search
CPC ................ A61F 2250/0096–2250/0098; A61F 2310/00131; A61F 2310/00257; A61F 2310/00544; A61F 2310/00658; A61L 31/18
USPC .................................. 623/1.34, 1.15; 424/9.4
See application file for complete search history.

(56) References Cited

U.S. PATENT DOCUMENTS

| | | | |
|---|---|---|---|
| 6,174,329 B1 * | 1/2001 | Callol et al. | 623/1.34 |
| 2008/0103594 A1 * | 5/2008 | Loffler et al. | 623/11.11 |
| 2011/0130822 A1 * | 6/2011 | Cottone | 623/1.15 |

FOREIGN PATENT DOCUMENTS

| | | |
|---|---|---|
| DE | 102006038238 A1 | 2/2008 |
| DE | 102008043642 A1 | 5/2010 |
| EP | 0824900 A2 | 2/1998 |

OTHER PUBLICATIONS

EP11185357.8 European Search Report mailed Jul. 30, 2014.

* cited by examiner

*Primary Examiner* — Christopher D Prone
(74) *Attorney, Agent, or Firm* — Wagenknecht IP Law Group PC

(57) ABSTRACT

A marker composite for medical implants composed of a biocorrodible metallic material and a medical implant comprising an X-ray marker which was made of the marker composite. The marker composite contains a large number of particles composed of a radio-opaque metal, which are embedded in an electrically non-conductive polymer. The particles have an additional electrically non-conductive coating.

12 Claims, 1 Drawing Sheet

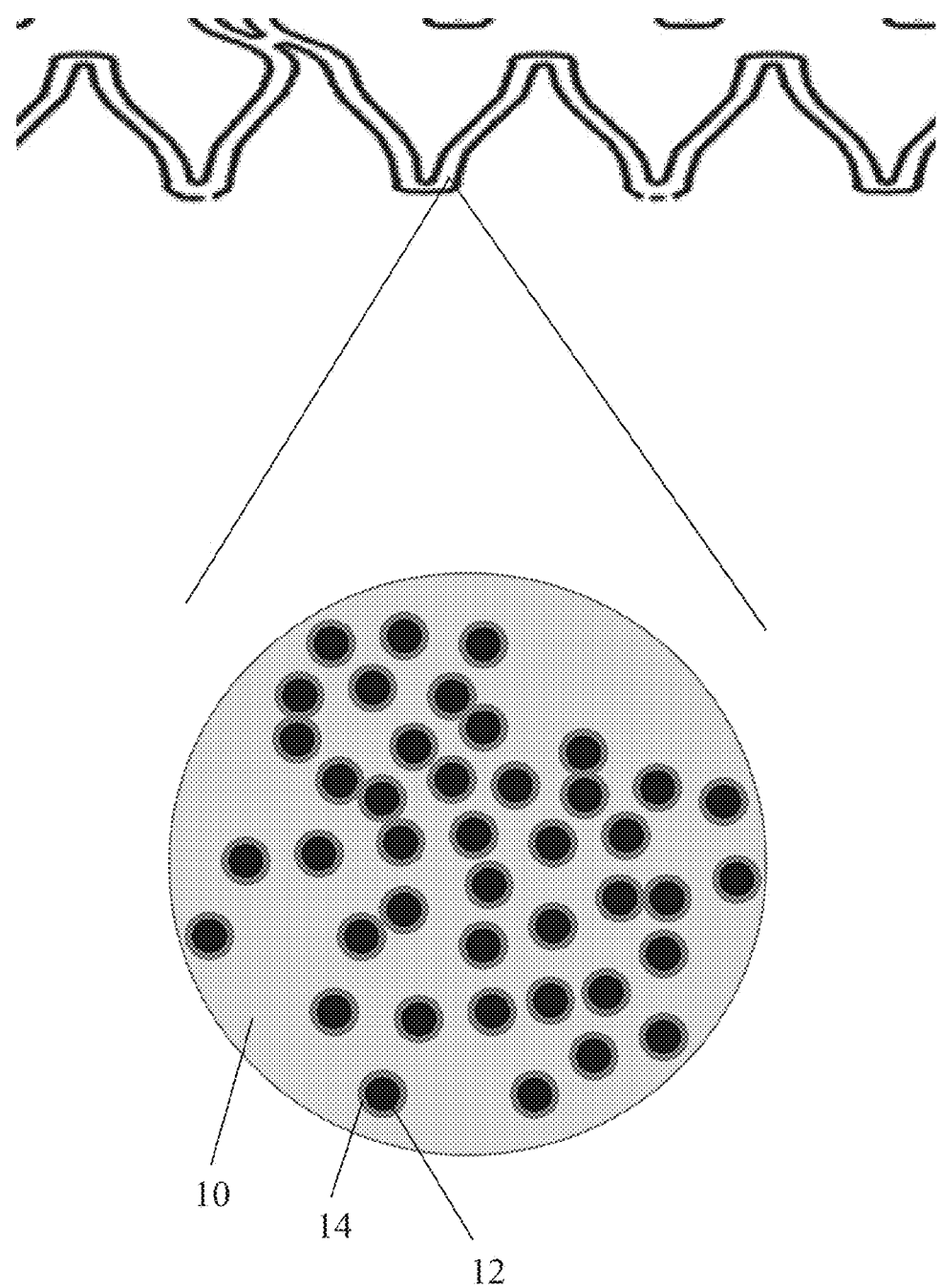

MARKER COMPOSITE AND MEDICAL IMPLANT COMPRISING AN X-RAY MARKER

CROSS REFERENCE TO RELATED APPLICATION

This patent application claims the benefit of U.S. Provisional Patent Application No. 61/410,976, filed on Nov. 8, 2010, which is hereby incorporated by reference in its entirety.

TECHNICAL FIELD

The invention relates to a marker composite for medical implants composed of a biocorrodible metallic material, and a medical implant composed of a biocorrodible metallic material comprising an X-ray marker which is composed of or was made of the marker composite.

BACKGROUND

Implants are utilized in modern medical technology in a variety of embodiments. They are used e.g. to support vessels, hollow organs, and ductal systems (endovascular implants e.g. stents), to attach and temporarily fix tissue implants and tissue transplants in position, and for orthopedic purposes such as pins, plates, or screws. The stent is a form of an implant that is used particularly frequently.

Stent implantation has become established as one of the most effective therapeutic measures for treating vascular disease. Stents are used to provide support in a patient's hollow organs. For this purpose, stents of a conventional design have a filigree support structure composed of metallic struts; the support structure is initially provided in a compressed form for insertion into the body, and is expanded at the application site. One of the main applications of stents of this type is to permanently or temporarily widen and hold open vasoconstrictions, in particular constrictions (stenoses) of the coronary arteries. In addition, aneurysm stents are known, for example, which are used to support damaged vascular walls.

Stents include a circumferential wall having a support force that suffices to hold the constricted vessel open to the desired extent; stents also include a tubular base body through which blood continues to flow without restriction. The circumferential wall is typically formed by a latticed support structure that enables the stent to be inserted, in a compressed state having a small outer diameter, until it reaches the constriction in the particular vessel to be treated, and to be expanded there, e.g. using a balloon catheter, until the vessel finally has the desired, enlarged inner diameter.

The implant, in particular the stent, has a base body composed of an implant material. An implant material is a nonliving material that is used for a medical application and interacts with biological systems. A prerequisite for the use of a material as an implant material that comes in contact with the physical surroundings when used as intended is its biocompatibility. "Biocompatibility" refers to the capability of a material to evoke an appropriate tissue response in a specific application. This includes an adaptation of the chemical, physical, biological, and morphological surface properties of an implant to the recipient tissue, with the objective of achieving a clinically desired interaction. The biocompatibility of the implant material is furthermore dependent on the time sequence of the response of the biosystem in which the implant is placed. For example, irritations and inflammations, which can cause tissue changes, occur over the relative short term. Biological systems therefore respond differently depending on the properties of the implant material. Depending on the response of the biosystem, implant materials can be subdivided into bioactive, bioinert, and degradable/resorbable materials.

Implant materials include polymers, metallic materials, and ceramic materials (as a coating, for example). Biocompatible metals and metal alloys for permanent implants contain e.g. stainless steels (e.g. 316L), cobalt-based alloys (e.g. CoCrMo casting alloys, CoCrMo forging alloys, CoCrWNi forging alloys, and CoCrNiMo forging alloys), pure titanium and titanium alloys (e.g. CP titanium, TiAl6V4 or TiAl6Nb7), and gold alloys. In the field of biocorrodible stents, the use of magnesium or pure iron and biocorrodible base alloys of the elements magnesium, iron, zinc, molybdenum, and tungsten is proposed. The present invention relates to biocorrodible base alloys, in particular base alloys of magnesium.

To perform radiological intraoperative and postoperative position monitoring, implants are provided with at least one marker if they are not already composed of a sufficiently radio-opaque material. The X-ray visibility of the marker is a function of the dimensions and X-ray absorption coefficient thereof. The X-ray absorption coefficient is, in turn, a function of the energy range of the X-ray radiation: it is typically 60 to 120 keV in the medical field, and 60 to 100 keV for coronary applications. The X-ray absorption coefficient typically increases as the atomic number in the periodic table rises and the density of the material increases. The presence of the marker should not restrict the functionality of the implant and/or be the starting point for inflammatory responses or rejection reactions of the body. Typically, for example, noble metals, such as gold and platinum, are used as marker materials.

The markers are provided (i) as solid material e.g. in the form of a coating, a strip, an inlay, or a molded body permanently bonded to the implant, or (ii) a powder embedded in a carrier matrix, in the form of a coating or as a filler material for a cavity in the implant. Variant (ii) can be implemented particularly easily in terms of production technology: A castable or sprayable mixture of the radio-opaque marker components and the material acting as a carrier matrix, possibly with a solvent added, is processed.

The biocorrodible metal alloys known from the prior art for use in medical implants have only slight X-ray visibility in the energy range of 60-100 keV, which is used for medical technology. However, X-ray diagnosis is an important instrument precisely for postoperative monitoring of the healing process or for checking minimally invasive interventions. Thus, for instance, stents have been placed in the coronary arteries during treatment of acute myocardial infarction for some years. The stent is positioned in the area of the lesion of the coronary vascular wall and prevents obstruction of the vascular wall after expansion. The procedure of positioning and expanding the stent must be continuously monitored by the cardiologist during the procedure.

For implants composed of biocorrodible metallic materials based on magnesium, iron, or tungsten, there are increased requirements on the marker material, which include:
 the marker is not to be detached prematurely from the base body of the implant by the corrosive processes, to avoid fragmentation and thus the danger of embolization;
 the marker is to have sufficient X-ray density even when material thicknesses are low, and
 the marker material is to have no or, at most, a slight influence on the degradation of the base body.

However, when markers are used that are composed of metallic materials on biocorrodible metallic base bodies, the particular problem arises that, due to electrochemical interactions between the two metallic materials, the degradation of the base body is altered in a contact region between the marker and the base body, i.e. the degradation is typically accelerated. DE 10 2008 043 642 A1 describes an endoprosthesis comprising a voluminous marker provided with a barrier layer, using which the radio-opaque material of the marker is electrically insulated from the base body. The base body can be composed of a biocorrodible magnesium alloy.

SUMMARY

The object of the present invention is to eliminate or at least diminish one or more of the above-discussed problems of the prior art. The invention relates to a marker composite for medical implants composed of a biocorrodible metallic material. The marker composite contains a plurality and thus a large number of particles of a radio-opaque metal which are embedded in an electrically non-conductive polymer. The particles have an additional electrically non-conductive coating.

The invention is based on the finding that the application of a passivating protective layer on the metal particles of the marker further reduces or completely eliminates the risk of contact corrosion.

Any conventional radio-opaque metal mentioned in the context of implants can be used as the radio-opaque metal for the marker. The marker component is present in the carrier matrix in suspended form. The metal is preferably an element selected from the group consisting of gold, iridium, platinum, and tantalum. The particles are composed of tantalum in particular.

The particles preferably have a mean particle size of 0.2 μm to 10 μm. The use of finely powdered metal particles simplifies the processing and application of the marker composite onto the implant, and the introduction of the marker composite into a cavity of the implant. The carrier matrix reduces a contact surface between the metallic marker components and the base body of the implant, thereby preventing or at least reducing unwanted interactions in regard to the corrosion behavior. The area of the implant which is to carry the marker is preferably coated with a small quantity of the carrier matrix (or with another polymer) before the marker is applied. After application of the marker composite, the cavity can be coated with a polymer once more to provide additional insulation.

The particle coating or layer is preferably composed of a carbide or oxide of the radio-opaque metal e.g. tantalum carbide or tantalum oxide. The creation of oxide layers or carbide layers on the surface of metal particles has been known for some time and will therefore not be discussed in greater detail here. Particles of Ta can be oxidized by exposure to air at 500 to 600° C. for 1 to 3 hours. Metallic tantalum is oxidized to form tantalum(V) oxide by the reaction with atmospheric oxygen. The lower oxides are formed only during the oxidation of tantalum or tantalum compounds, in fact $TaO_x$ ($Ta_6O$) forms at approximately 300° C., $TaO_y$ ($Ta_4O$) forms below 500° C., TaO and $TaO_2$ form as intermediate layers between the metal and $Ta_2O_5$ when tantalum is oxidized to form $Ta_2O_5$. Due to the high enthalpy of formation of tantalum oxide, interaction with the surrounding bodily fluid is low.

This low interaction is substantially superposed by the chemical reactions between the Mg implant and the bodily fluid, and is therefore insignificant in regard to the solution according to the invention.

As an alternative, the coating can be composed preferably of Parylene.

The polymer of the carrier matrix is preferably selected from the group comprising polyurethanes, silicones, poly (butyl methacrylates), cyanoacrylates, and epoxy resins.

A further aspect of the invention is that of providing a medical implant composed of a biocorrodible metallic material that comprises an X-ray marker composed of a marker composite that has the aforementioned composition or is made of this marker composite. In the latter case, for example, the marker composite is hardened after it is inserted into a cavity or applied as a coating.

Within the scope of the invention, implants are devices introduced into the body using a surgical procedure, and comprise fastening elements for bone, such as screws, plates, or nails, surgical suture material, intestinal clamps, vascular clips, prostheses in the area of hard and soft tissue, and anchoring elements for electrodes, in particular of pacemakers or defibrillators.

The implant is preferably a stent. Stents of a conventional design have a filigree support structure composed of metallic struts; the support structure is initially provided in an unexpanded state for insertion into the body, and is then widened into an expanded state at the application site.

Within the scope of the invention, those alloys are referred to as being biocorrodible that degrade/convert in a physiological environment, and therefore the part of the implant composed of the material is no longer present or at least substantially no longer present.

Biocorrodible alloys comprise biocorrodible base alloys of the elements magnesium, iron, zinc, molybdenum, and tungsten. Magnesium is preferred. In this context, a base alloy is understood to be a metallic microstructure having one of the elements magnesium, iron, zinc, molybdenum, and tungsten as the main component. The main component is the alloy component that comprises the largest percentage by weight of the alloy. A percentage of the main component is preferably more than 50% by weight, in particular more than 70% by weight. The composition of the alloy is to be selected such that the alloy is biocorrodible. Artificial plasma, as has been previously described according to EN ISO 10993-15:2000 for biocorrosion assays (composition NaCl 6.8 g/l, $CaCl_2$ 0.2 g/l, KCl 0.4 g/l, $MgSO_4$ 0.1 g/l, $NaHCO_3$ 2.2 g/l, $Na_2HPO_4$ 0.126 g/l, $NaH_2PO_4$ 0.026 g/l), is used as a testing medium to test the corrosion behavior of an alloy under consideration. A sample of the alloy to be investigated is stored in a closed sample container with a defined quantity of the testing medium at 37° C. At time intervals defined according to the anticipated corrosion behavior, of a few hours up to multiple months, the samples are removed and examined for traces of corrosion in a known manner. The artificial plasma according to EN ISO 10993-15:2000 corresponds to a medium similar to blood and thus represents a possibility for reproducibly simulating a physiological environment within the scope of the invention.

DESCRIPTION OF THE DRAWING

FIG. 1 shows an enlarged, schematic sectional view of a marker composed of the marker composite according to the invention.

DETAILED DESCRIPTION

The invention is explained in greater detail below with reference to an embodiment.

Embodiment 1

FIG. 1 shows a cross section, which has a diameter of approximately 300-400 μm, of a disk-shaped marker composed of the marker composite according to the invention. Matrix 10 is composed of an epoxy resin in which tantalum particles 12 having a diameter of approximately 10 μm are embedded. Particles 12 have a percentage by weight of more than 80% of the marker. Particles 12 have a tantalum oxide layer 14 on their surface.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A medical implant composed of a biocorrodible metallic material and comprising an X-ray marker which is composed of or is made of a marker composite comprising a plurality of particles of a radio-opaque metal, each individual particle coated with a coating selected from the group consisting of an oxide coating, a carbide coating, and a parylene coating such that the each of the plurality of particles are separated from one another by the coating, and wherein the coated particles are embedded in an electrically non-conductive polymer as a carrier matrix, wherein the carrier matrix is positioned between the biocorrodible metallic material and each of the plurality of coated particles to prevent contact between the biocorrodible metallic material and each of the plurality of coated particles.

2. The medical implant according to claim 1, wherein the implant is a stent.

3. The medical implant according to claim 1, wherein the biocorrodible metallic material is a magnesium alloy.

4. The medical implant according to claim 1, wherein the X-ray marker is present in the form of a coating or a cavity filling.

5. The medical implant according to claim 1, wherein the radio-opaque metal is composed of an element selected from the group consisting of gold, iridium, platinum, and tantalum.

6. The medical implant according to claim 5, wherein the element is tantalum.

7. The medical implant according to claim 1, wherein the coating is the oxide or carbide coating and is an oxide or carbide of the radio-opaque metal.

8. The medical implant according to claim 1, wherein the polymer is selected from the group consisting of a polyurethane, a silicone, a poly(butyl methacrylate), a cyanoacrylate, and an epoxy resin.

9. A marker composite for a medical implant composed of a biocorrodible metallic material, wherein the marker composite comprises a plurality of individual particles suspended in an electrically non-conductive carrier matrix formed from a polymer, wherein each particle is of a radio-opaque metal individually coated with a coating selected from the group consisting of a carbide of the radio-opaque material, an oxide of the radio-opaque metal, and parylene, thereby preventing contact between the radio-opaque metal of different particles.

10. The marker composite according to claim 9, wherein the carrier matrix provides a protective coating that prevents contact between each of the plurality of particles and the metallic material of the implant, and the radio-opaque metal is composed of an element selected from the group consisting of gold, iridium, platinum, and tantalum.

11. The marker composite according to claim 10, wherein the radio-opaque metal is tantalum.

12. The marker composite according to claim 9, wherein the polymer is selected from the group consisting of a polyurethane, a silicone, a poly(butyl methacrylate), a cyanoacrylate, and an epoxy resin.

* * * * *